United States Patent
Hertz et al.

[11] Patent Number: 6,090,048
[45] Date of Patent: Jul. 18, 2000

[54] METHOD AND ARRANGEMENT FOR DETECTING THE CONDITION OF A BLOOD VESSEL ACCESS

[75] Inventors: Thomas Hertz, Lund; Sven Jönsson, Staffanstorp; Jan Sternby, Lund, all of Sweden

[73] Assignee: Gambro AB, Sweden

[21] Appl. No.: 09/029,813

[22] PCT Filed: Sep. 11, 1996

[86] PCT No.: PCT/SE96/01127

§ 371 Date: Mar. 10, 1998

§ 102(e) Date: Mar. 10, 1998

[87] PCT Pub. No.: WO97/10013

PCT Pub. Date: Mar. 20, 1997

[30] Foreign Application Priority Data

Sep. 12, 1995 [SE] Sweden ................... 9503125

[51] Int. Cl.[7] ........................... A61B 5/02; A61M 37/00; A61M 1/00
[52] U.S. Cl. ............... 600/485; 604/4; 604/27; 604/31; 600/486
[58] Field of Search ............ 600/485, 486, 600/487; 604/4, 5, 6, 65, 67, 27, 31, 29, 28

[56] References Cited

U.S. PATENT DOCUMENTS

| | | | |
|---|---|---|---|
| 3,882,861 | 5/1975 | Kettering et al. | 604/4 |
| 4,231,366 | 11/1980 | Schael | 604/50 |
| 4,353,368 | 10/1982 | Slovak et al. | 604/50 |
| 4,534,756 | 8/1985 | Nelson | 604/50 |
| 4,648,869 | 3/1987 | Bobo, Jr. | 604/49 |
| 4,710,163 | 12/1987 | Butterfield | 604/65 |
| 4,828,543 | 5/1989 | Weiss et al. | 604/4 |
| 4,846,792 | 7/1989 | Bobo, Jr. et al. | 604/50 |
| 4,959,050 | 9/1990 | Bobo, Jr. | 604/49 |
| 4,979,940 | 12/1990 | Bobo, Jr. et al. | 604/50 |
| 4,981,467 | 1/1991 | Bobo, Jr. et al. | 604/65 |
| 5,580,460 | 12/1996 | Polaschegg | 210/646 |

FOREIGN PATENT DOCUMENTS

| | | |
|---|---|---|
| 0 121 931 | 10/1984 | European Pat. Off. . |
| 0 328 162 | 8/1989 | European Pat. Off. . |
| 0 328 163 | 8/1989 | European Pat. Off. . |
| 0 332 330 | 9/1989 | European Pat. Off. . |
| 0 330 761 B1 | 8/1993 | European Pat. Off. . |
| 24 45 403 | 4/1975 | Germany . |

*Primary Examiner*—Cary O'Connor
*Assistant Examiner*—Navin Natnithithadha
*Attorney, Agent, or Firm*—Lerner, David, Littenberg, Krumholz & Mentlik, LLP

[57] ABSTRACT

Methods for detecting the condition of a catheter providing access to a patient's blood vessel are disclosed in which the blood is supplied to an extracorporeal blood flow circuit. The method includes generating a pressure wave on one side of one of the access points for supplying blood to the extracorporeal blood flow circuit or returning the blood to the patient, then sensing the pressure wave on the other side of the access points. Apparatus for detecting the condition of the catheter are also provided.

26 Claims, 3 Drawing Sheets

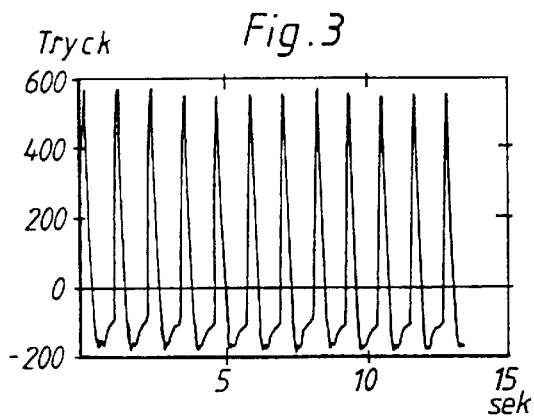
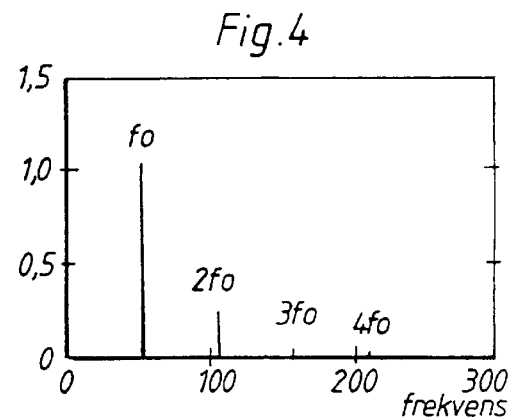
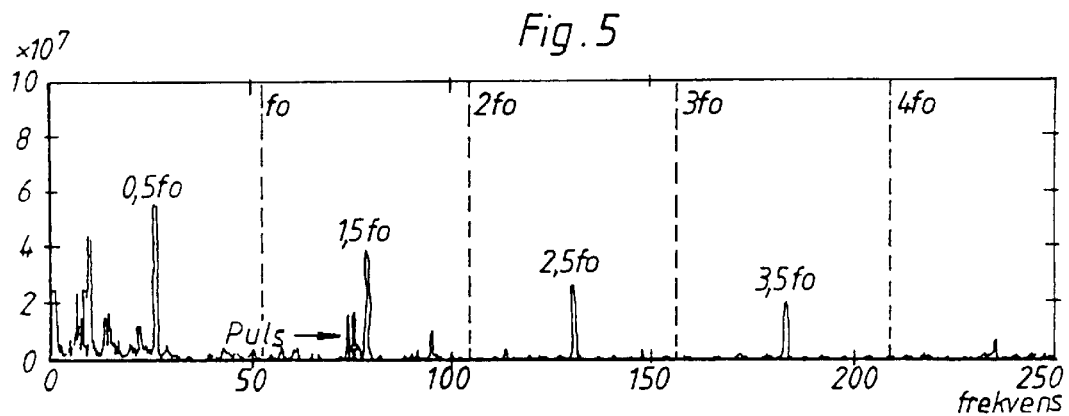
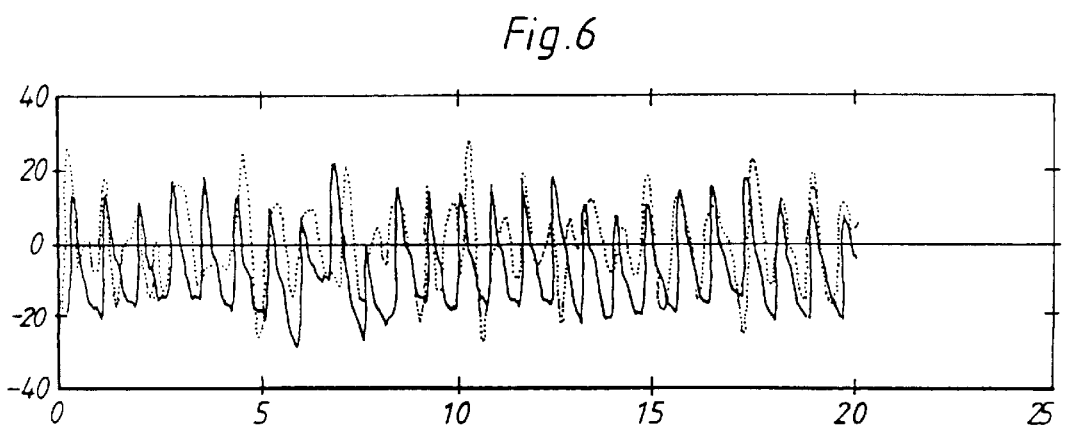

METHOD AND ARRANGEMENT FOR DETECTING THE CONDITION OF A BLOOD VESSEL ACCESS

FIELD OF THE INVENTION

The present invention relates to a method for detecting the condition of a blood vessel access in connection with extracorporeal blood treatments such as hemodialysis, hemodiafiltration, hemofiltration, plasmapheresis or similar treatments. The present invention also relates to an apparatus for carrying out such a method.

BACKGROUND OF THE INVENTION

Access to a blood vessel is generally obtained by introduction of a needle or a catheter into a vein.

With hemodialysis, blood vessel access constitutes one or more needles or catheters, through which blood is taken out to an extracorporeal blood circuit where the treatment occurs. With hemodialysis the blood normally passes through the extracorporeal blood circuit at a relatively high speed, on the order of up to 500 ml/min. Blood is normally taken out through an arterial needle and reintroduced into the body through a venous needle. Hemodialysis using a single needle (single needle dialysis) or catheters also exists.

If the blood vessel access, such as the arterial needle and/or the venous needle, is not placed correctly, malfunctions can occur.

If the arterial needle is positioned too close to the walls of the blood vessel, it can be difficult to achieve sufficient blood flow with the available pump capacity. If the arterial needle is placed outside the blood vessel, the needle will become blocked by the tissues, and no blood flow will be obtained at all. If the arterial needle is outside the body, air will be sucked into the circuit. These conditions are relatively simple to detect in the extracorporeal blood circuit.

If, however, the venous needle is unintentionally loosened, a life-threatening situation can rapidly arise, since the patient can lose a large amount of blood in a short period of time.

With hemodialysis, the dialysis machine is provided with a plurality of detectors which detect dangerous conditions, and which activate clamp devices which stop the extracorporeal blood flow when such dangerous conditions arise.

Normally the dialysis machine is provided with an arterial pressure sensor which measures the pressure in the extracorporeal blood circuit upstream of the circulation pump. An underpressure of between −20 mm Hg and −80 mm Hg is normally present even though levels as low as −200 mm Hg can be produced with large blood flows. If the pressure approaches atmospheric pressure, this indicates that air is being sucked into the system, while an underpressure which is much too low (below about −200 mm Hg) indicates that the arterial needle can be blocked or not properly inserted into the blood vessel or fistula. Other causes can be that the arterial tube is kinked or that the fistula has collapsed due to an incorrect arm position.

The dialysis machine is further provided with a venous pressure sensor downstream of the dialyser, but before the venous needle, normally in connection with a venous drip chamber where the venous pressure is normally between +50 and +150 mm Hg. The pressure can vary depending on the size of the venous needle, variations in the blood flow and the composition of the blood, blocking of the venous needle or the venous blood tubes, or a separate venous blood filter which is often present in the drip chamber. Additional causes can be that the venous needle is unsuitably placed or that the venous tube is kinked. Further causes are changes in the height location of the fistula, for instance if the patient is sitting or lying.

If the venous needle comes out of the fistula, a reduction of pressure at the venous sensor will occur, which can be detected. This detection is, however, rather uncertain. If the tube is moved upwardly through a holder and the end gets stuck higher up than the arm, the pressure in the venous sensor might not be reduced at all, or only reduced insignificantly so that a set alarm level is not reached. Additionally, it may happen that the venous needle comes out when the patient turns, at the same time there being a risk that the patient will lie on the tube so that it is completely or partially blocked, or that the tube will kink.

There is therefore a desire to have a separate means of detecting whether the needle, used in connection with hemodialysis or another extracorporeal blood treatment, is still adequately in position at the blood access site, and in this respect in particular the venous needle.

This problem has previously been solved by providing the venous needle and/or the arterial needle with some form of sensor which detects if the needles move from a predetermined position. One example is to provide the needles with magnets and arrange the sensors on the arm which senses whether said magnets are close to the sensors. Another method would be to provide the arm with a conductivity detector which provides a signal if blood leaks out. The disadvantage with such detectors is that they have to be attached to the patient and simultaneously be electrically connected to the dialysis machine in order to stop the blood pump and disengage the extracorporeal circuit during malfunction.

With catheters for blood vessel access, clogging may occur or the catheter's opening may be located too close to the blood vessel's wall and get stuck due to suction.

European Patent No. 121,931 discloses an apparatus and method for use in a parenteral administration systems for detecting fault conditions. In one embodiment thereof, the fault detection uses high pass filtering of the pressure signals to pass only the signal components attributable to a patient's heartbeat. An alarm signal is thus produced whenever a dropout in the heartbeat pulses is detected.

European Patent No. 332,330 discloses an infusion system for infusing a fluid into a patient comprising an infusion device for delivering the fluid in both a normal delivery pattern and a test pulse, and a conduit for conducting the fluid from the infusion device to the patient. The test pulse creates a pressure wave response in the conduit. Abnormal diffusion can thus be detected by determining the area between a base line and at least a portion of a pressure versus time curve representing the pressure wave respons.

SUMMARY OF THE INVENTION

The object of the present invention is to provide a method and an apparatus for detecting the condition of a blood vessel access, which detection is safe, reliable and simple.

In accordance with the present invention, these and other objects have now been realized by the invention of a method of detecting the condition of a catheter providing access to a patient's blood vessel for supplying blood to a first access point in an extracorporeal blood flow circuit including a blood pump and returning said blood to a second access point in the extracorporeal blood flow circuit for return to the patient's blood vessel, the method comprising generating a pressure wave on one side of one of the first and second access points and sensing the pressure wave on the other side of the one of the first and second access points. In a preferred embodiment, the pressure wave has a frequency of between about 0.2 and 20 Hz.

In accordance with one embodiment of the method of the present invention, generating of the pressure wave is carried out by means of a pressure wave generator comprising the patient's heart. In a preferred embodiment, sensing of the pressure wave is carried out in the extracorporeal blood flow circuit.

In accordance with another embodiment of the method of the present invention, /generating of the pressure wave is carried out by means of a pressure wave generator comprising the blood pump, whereby sensing of the pressure wave is carried out through the access to the patient's blood vessel. In accordance with a preferred embodiment, the method includes processing the pressure wave sensed by the pressure sensor comprising subtracting a signal corresponding to a pressure wave obtained from the blood pump whereby a pressure signal corresponding to the patient's heartbeat is obtained.

In accordance with another embodiment of the method of the present invention, the extracorporeal blood flow circuit includes a dialyzer, whereby the pressure wave passes through the dialyzer thereby sensing an altered condition of the dialyzer therein.

In accordance with the apparatus of the present invention, apparatus is provided for detecting the condition of a catheter providing access to a patient's blood vessel comprising an extracorporeal blood flow circuit for receiving the patient's blood including a first access point for receiving the blood and a second access point for returning the blood to the patient's blood vessel, the extracorporeal blood flow circuit including a blood pump, a pressure wave generator for generating a pressure wave on one side of one of the first and second access points, and a pressure sensor for sensing the pressure wave on the other side of the one of the first and second access points.

In accordance with one embodiment of the apparatus of the present invention, the pressure wave generator produces pressure waves having a frequency of between about 0.2 and 20 Hz.

In accordance with another embodiment of the apparatus of the present invention, the pressure wave generator comprises a patient's heart, and the pressure sensor is arranged in the extracorporeal blood flow circuit.

In accordance with another embodiment of the apparatus of the present invention, the pressure wave generator comprises the blood pump, whereby the pressure wave passes to the pressure sensor through the catheter. In a preferred embodiment, processing means are provided for processing the pressure wave by subtraction of a pressure signal corresponding to a pressure wave obtained from the blood pump in order to obtain a pulse signal corresponding to the patient's heartbeat.

The present invention is based on the integrity of the blood vessel access being detectable by transmission of a pressure wave from one side of the blood vessel access to the other side. There is thus a pressure wave generator on one side of the blood vessel access and a detection device on the other side.

In a preferred embodiment, the patient's heart is used as the pressure wave generator, while a pressure sensor is arranged on the other side of the blood vessel access, i.e. in the tube which leads from the catheter or the needle outwardly towards the patient. A separate pressure wave generator can of course also be arranged on the patient, for example in the form of an armband provided with a pressure wave generator which presses against the surface of the skin, for instance at the wrist.

A suitable frequency for the pressure wave generator is about 0.2 Hz to about 20 Hz. By "pressure wave" is meant the type of pressure wave which is produced by a pump or the heart and can comprise sound, in particular infrasound. The present invention uses the transmission of a pressure wave or infrasound through a fluid, such as blood, and the vessels or tubes and the apparatus which is connected thereto, which also includes passage through air.

In connection with an extracorporeal circuit with an arterial needle and a venous needle, an existing blood pump in the extracorporeal blood circuit can be used as the pressure wave generator, said blood pump generating powerful pressure waves. With hemodialysis, it is common to use a peristaltic pump which produces similar pressure waves. This pressure wave passes from the blood pump through the arterial needle to the blood vessel as well as through the blood vessel to the venous needle and from there to a pressure sensor arranged in connection with the venous needle. Through signal analysis at the pressure sensor it can be established whether the path for the pressure wave through the blood vessel access disappears or changes radically, which is an indication of a modified condition of the blood vessel access.

With the above-mentioned extracorporeal blood circuit, the heart can also be used as the pressure wave generator and the pressure wave can be detected after the blood vessel access in order to detect the integrity or the condition of these needles. In this case it is necessary to filter the signal which is obtained from the pressure sensor in order to remove pressure waves from other sources than the heart, such as from the blood pump.

Different methods for determining whether or not an alarm signal should be produced are also described.

BRIEF DESCRIPTION OF THE DRAWINGS

The invention will now be described in more detail with reference to the accompanying drawings.

FIG. 3 is a graphical representation showing the pressure signal from an arterial sensor.

FIG. 4 is a graphical representation showing the pressure signal in FIG. 3 resolved in the frequency plane.

FIG. 5 is a graphical representation corresponding to FIG. 4, after filtering of the signal.

FIG. 6 is a graphical representation showing the pressure signal from the arterial sensor after filtering.

DETAILED DESCRIPTION OF PREFERRED EMBODIMENTS

Figure 1:
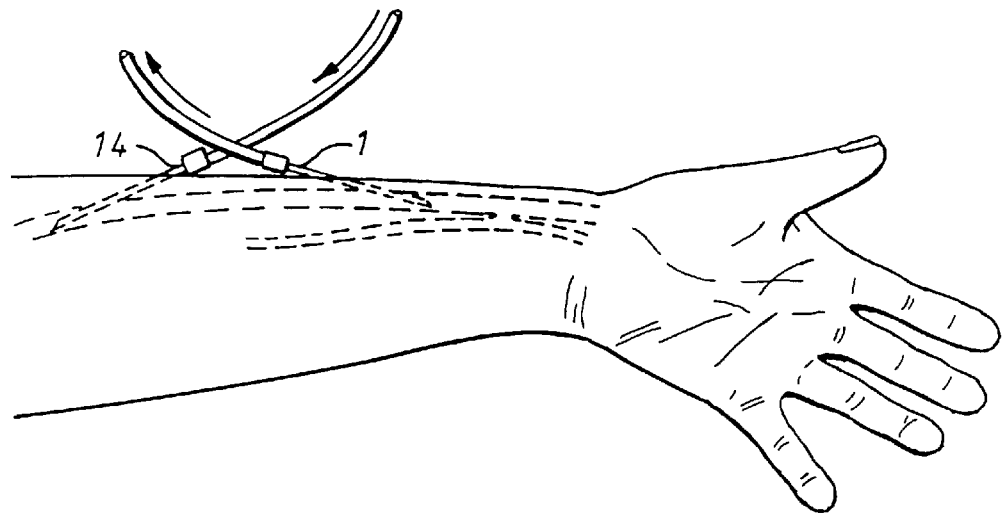
FIG. 1 is a side, perspective view, showing an arm provided with a fistula intended for dialysis.

Referring to the Figures, in which like reference numerals refer to like elements thereof, FIG. 1 shows the left arm of a patient provided with a fistula suitable for hemodialysis. A fistula has shown itself to be the most effective, durable, permanent blood vessel access for extracorporeal blood treatment.

A fistula is created by surgical intervention, whereby a connection is formed between an artery and a proximate vein, for example in the lower arm. The fistula is formed either by an opening being formed from the sidewall of the artery to the sidewall of the vein as shown in FIG. 1, or by an opening in the sidewall of the artery being connected with the end of a vein. By means of the fistula, the blood flow in the artery is short-circuited to the vein, which leads to an arterializing of the vein and an increased bloodflow in the vein which allows taking out of bloodflows up to 500 ml/minute or more.

As is clear from FIG. 1, the arterial needle which leads to the extracorporeal circuit is always placed in the part of the arterialized vein which faces the hand, but at least three centimeters downstream of the connection between the artery and the vein. The arterial needle can either point towards the hand as shown in FIG. 1 or in the other direction. The venous needle is to be inserted directed towards the heart, approximately five centimeters from the arterial needle.

The expression "fistula" will be used below for the part of the arterialized vein where the needles are inserted.

Other types of blood vessel access can be used, such as a Scribner-shunt or one or more catheters.

Figure 2:
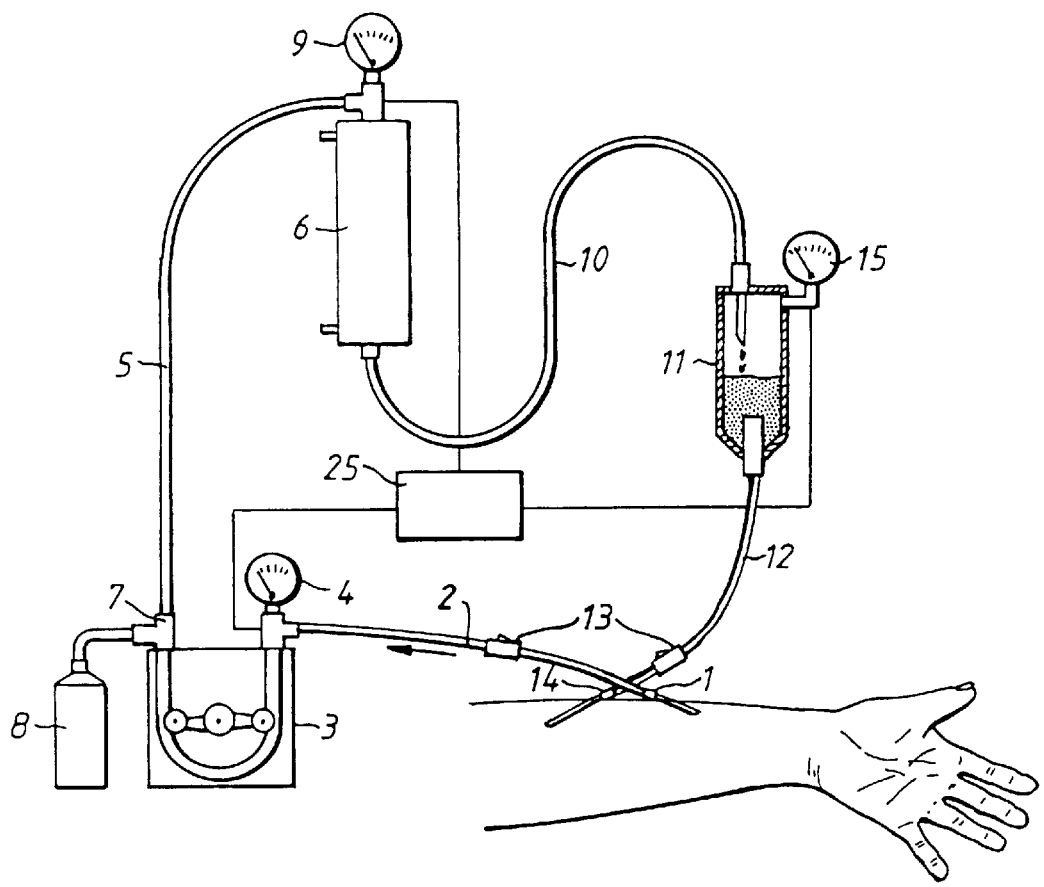
FIG. 2 is a side, elevational, schematic view, showing the extracorporeal blood circuit in a conventional dialysis machine.

FIG. 2 shows an extracorporeal circuit of the type which is used in a dialysis machine. The circuit comprises an arterial needle 1 and an arterial tube 2 which connects the arterial needle 1 to a blood pump 3 which is normally of the peristaltic type, such as indicated in FIG. 2. At the inlet of the pump there is an arterial sensor 4 which measures the pressure immediately before the pump in the arterial tube 2. The blood pump 3 leads the blood further, through tube 5, to a dialyser 6. The tube 5 can comprise an inlet 7 for heparin connected to a heparin pump 8. Many dialysis machines are additionally provided with a pressure sensor 9 which measures the pressure between the blood pump 3 and the dialyser 6, i.e., the so-called system pressure. The blood is lead through tube 10 from the dialyser 6 to a venous drip chamber 11 and from there back to the patient through a venous tube 12 and a venous needle 14. The venous tube 12 is provided with a clamp device 13 which stops the blood flow upon the occurrence of a malfunction. The venous drip chamber 11 is provided with a venous sensor 15 which measures the pressure in the venous drip chamber. The arterial tube 2 can also be provided with a clamp device similar to the clamp device 13. Both the arterial needle 1 and the venous needle 14 are inserted into the fistula.

When the blood passes the arterial needle 1, which has as small a cross-sectional area as possible so as not to damage the fistula, the pressure sinks to between about −20 to −80 mm Hg, which is measured by the arterial sensor 4. The pressure rises in the pump 3, said pressure being measured by the system sensor 9. In the dialyser 6, the pressure falls due to the flow resistance therein and the pressure downstream of the dialyser is measured with the venous sensor 15, normally in the venous drip chamber. The pressure in the venous drip chamber is normally between about +50 to +150 mm Hg. Finally the blood is released to the fistula through the venous needle 14, whereby a pressure drop occurs in the needle due to the flow through its small cross-section.

The aforementioned pressure conditions vary considerably from patient to patient and can even vary for one and the same patient between different treatment sessions. It is therefore difficult to set up limit values for the pressure sensors which indicate different error conditions. It is particularly difficult to indicate whether the venous needle 14 is coming out of the fistula, particularly if the venous tube 12 is hanging over a position so that the venous needle is moved upwardly a long way when it comes out.

In many dialysis machines one or more of said pressure detectors are not present. Normally however there will be at least one veneous pressure sensor.

FIG. 3 shows a pressure curve which is obtained from the arterial sensor 4 in FIG. 2. This pressure curve corresponds to the pressure curve of the blood pump 3 on its suction side. The pressure pulses emanate from the periods of time when one pressure roller takes over from the other pressure roller, i.e. showing the pump stroke.

The pressure curve in FIG. 3 corresponds to the blood pump's suction stroke, but also has a superimposed pulse signal obtained from the pulse in the fistula. This pulse signal is, however, very insignificant and cannot be observed with the naked eye in FIG. 3.

In FIG. 4, the pressure curve in FIG. 3 has been resolved in the frequency plane (Fourier-transformation). It can be seen that the signal consists of a base frequency, fo, at about 52 strokes per minute, as well as a large number of harmonics, of which only three can be identified in FIG. 4.

By eliminating the frequency fo and its harmonics, the effect of the blood pump's pressure pulses on the pressure in the arterial sensor 4 can be eliminated. Such elimination can be done with the aid of notch filters.

If the frequency and phase of the interference are known, notch-equivalent filters can advantageously be used. One example is the generation of sinus signals at the known frequency together with its harmonics and the subtraction of these from the signal at suitable phase. With an adaptive filter, the amplitude and the phase of the generated signals can be determined. This filter technique is known. The calculations and the subtraction suitably occur in a signal processor. The signal processor and its analogue/digital converter must however have high resolution since the pulse signal is very weak.

FIG. 5 shows the signal in FIG. 3 in the frequency plane after subtraction of the interference due to the blood pump's pressure waves, i.e. subtraction of the base frequency fo and its harmonics. From FIG. 5 it can be seen that a half base frequency, i.e. 0.5 fo, is also represented in the frequency plane together with the corresponding harmonics 1.5 fo, 2.5 fo, 3.5 fo etc. (fo, 2fo, 3fo etc. have already been eliminated). This half base frequency is due to the fact that the blood pump used is of the peristaltic type, with two rollers which act on the tube segment in the blood pump. The rollers are probably not entirely symmetrical, which gives rise to the half base frequency (0.5 fo).

Half the base frequency is also the same as the motor's rotational speed. This rotational speed is known since it is generated by the dialysis machine. The motor which drives the blood pump can be constituted by a stepping motor which is driven at predetermined frequency. By using this known frequency signal or the known rotational speed of the blood pump, the frequency fo can be determined very accurately, which results in an accurate removal of these frequency components.

FIG. 6 shows the signal which is obtained after the above-mentioned adaptive filtering and elimination of the pump frequency and its harmonics. Moreover, the pulse signal has passed a band-pass filter which lets through the frequencies 30–180 strokes/minute (0.5–3 Hz). As is clear from FIG. 6, the amplitude of the pulse signal is dependent on many factors, such as damping in the tubes, etc. Other factors can be changes in the height position of the arm, or that the needle has temporarily come closer to the wall of the fistula.

Even though FIGS. 3–6 relate to the pressure conditions of the arterial needle, the conditions are similar with a venous needle.

An indication that the needle has fallen out is that the amplitude of the pulse signal sinks to zero. In practice, an alarm signal can be emitted if the amplitude sinks below 20% of an earlier determined normal amplitude. This normal amplitude can be determined during the first stage of the treatment when the dialyser is being observed by a nurse, for example during the first half hour of the treatment.

The pulse signal can disappear temporarily for other reasons than the needle having fallen out, such as the patient moving. The adaptive signal processing then re-adjusts the settings to the new situation, after which the pulse signal can be recovered and separated. Such an adaptive adjustment to normal, but changed situations, takes a certain amount of time. It is therefore suitable if the emitting of an alarm signal is delayed by a short period of time on the order of a number seconds.

Another way of determining when an alarm signal is to be emitted is to determine the relationship between the amplitude of the pulse signals from the venous sensor 15 and the pulse signal from the arterial sensor 4. Due to the different damping in, for instance, the blood tube 2 and the blood tube 12, respectively, as well as the venous drip chamber 11, the amplitude from these sensors is different, whereby the venous sensor 15 generally has a lower amplitude.

If the pulse signal from the venous sensor 15 disappears more or less completely at the same time as the pulse signal from the arterial sensor 4 is still present and substantially unchanged, this is a certain sign of a problem with the venous needle 14; either that it has come too close to the blood vessel wall or fallen out completely. According to the present invention it is proposed that the alarm signal is emitted when the relationship between the amplitudes for the pulse signals from the venous sensor 15 and the arterial sensor 4, respectively, are changed substantially, such as the relationship between the amplitudes sinking below a limit value which is 50% of the original value. If it is desired to obtain greater accuracy for the detection, said limit value can instead be set at 30%. If there is a patient who has weak blood vessels, whereby it can easily happen that the venous needle 14 comes too close to the blood vessel wall, or if problems arise in another way which can be acceptable and would not lead to an alarm, the limit value should be set even lower, such as at 20%.

If the amplitude of the pulse signal from the arterial sensor 4 reduces greatly, this is probably an indication of a problem with the arterial needle 1 which can also give rise to an alarm signal.

From FIG. 5 it can be seen that if the frequency of the pulse lies close to the half base frequency (0.5 fo) of the blood pump or multiples thereof, difficulties will occur in separating the pulse signal from the blood pump signal. In particular, there will be difficulties in such a separation if the difference between the pulse and any of the blood pump's frequencies is less than about 5–10%. In accordance with the present invention, it is suggested that the blood pump is adapted so that the pulse always lies at at least about 10% from any of the blood pump's frequency components. This can be done by making the blood pump increase or decrease its speed by about ±10% when the pulse detection system according to the invention senses that there is a risk of collision. Such a change of the blood pump's speed will hardly be noticed by the patient. In order to reduce the risk of exceeding any maximum possible bloodflow speed, said regulation can be −15% to 5% or −20% to 0%, or something similar.

The frequency of the pulse signal can be used for other purposes such as are known per se. Thus, a great rise in the pulse implies that there is a risk for shock, etc.

Since the pressure pulses of the blood pump 3 are strong, these pressure pulses can be transmitted to the venous sensor 15 through a path which comprises the tube 2, the arterial needle 1, the fistula, the venous needle 14 and the tube 12 to the venous sensor 15. If the arterial needle 1 and/or the venous needle 14 comes out, said path for the pressure pulses will be broken and thus will cease. This characteristic can be used in order to detect the integrity of both the arterial needle and the venous needle simultaneously.

FIG. 2 shows a pressure sensor 9 for the system pressure. The pressure wave from the blood pump 3 passes through the system sensor 9 and the dialyser 6 to the venous sensor 15. In this way there is both a time delay from the system sensor 9 to the venous sensor 15 and a damping.

The system sensor 9 is positioned so that the pulse signal is very small or completely absent. By comparing the signals from the arterial sensor 4, the venous sensor 15 and the system sensor 9, suitable conditions for emitting an alarm signal can be determined.

Figure 7:
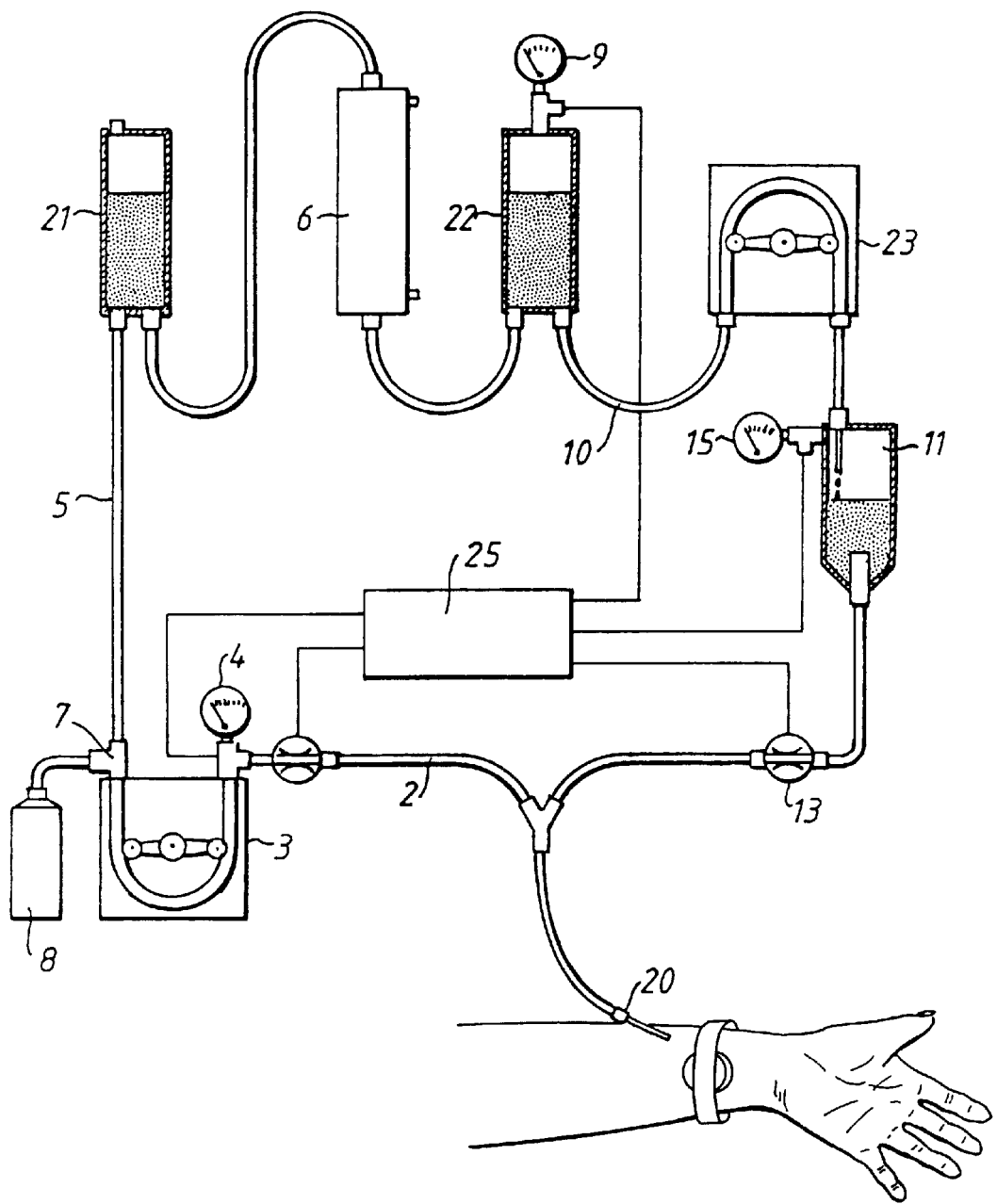
FIG. 7 is a side, elevational, schematic view showing the extracorporeal blood circuit with single needle dialysis.

FIG. 7 shows a schematic circuit similar to FIG. 2 for single-needle dialysis, whereby the same reference numerals have been used for the same components as in FIG. 2. The difference compared to two-needle dialysis is merely that one needle is used. Furthermore, expansion vessels 21 and 22 are required and often a second pump 23. The system pressure sensor 9 is often placed after the dialyser 6. Apart from this, the function is basically the same as described above, in as far as concerns the present invention.

Frequencies between about 0.2–20 Hz have been quoted above. The reason for the use of these frequencies is that they are in the infrasound range and do not give rise to audible sound. It is useful to use frequencies of about 1 Hz since many patients find this frequency calming, presumably due to the fact that it is close to the frequency of the heart. Normally, however, it is preferable to use frequencies for the blood pump which differ from the heart frequency if the pulse is to be used as an indication, for example 1.5 Hz and upwards or below about 0.8 Hz.

An ultrasound generator can also be used as the pressure wave generator, it being coupled to the blood vessel by an arm band as described above, or to the extracorporeal blood circuit for transmission through the blood vessel access as described above. A suitable ultrasound frequency ought to lie at just above 20 kHz, for instance 20–40 kHz. In principle, it is possible to use frequencies within the range of 20–20,000 Hz, but this is not preferred since it has apparently been found to be disturbing to the patients and personnel.

The principles of the present invention can also be applied for detecting the condition of another component in the extracorporeal circuit, such as the dialyser, by letting a pressure wave pass through that component, and detecting the changed condition with a pressure sensor.

The invention can also be used for other applications than those described in detail above, such as those mentioned in the introduction, like hemofiltration etc. The various electronic means for obtaining the desired function have not been described above although a skilled man will realise various possibilities and can practice the invention without a detailed account of any embodiments.

We claim:

1. A method of detecting the condition of an access device providing access to a patient's blood vessel for supplying blood to an introduction point in an extracorporeal blood flow circuit including a blood pump and returning said blood to a an exit point in said extracorporeal blood flow circuit for return to said patient's blood vessel via said access device, said method comprising generating a pressure wave on one side of said access device by arranging a pressure wave generator on the patient, sensing said pressure wave on the other side of said access device in said extracorporeal blood flow circuit, and indicating the condition of the access device by analysing a signal sensed on the other side of said access device for substantial disappearance of the signal.

2. The method of claim 1 wherein said pressure wave has a frequency of between about 0.2 and 20 Hz.

3. The method of claim 1, wherein said pressure wave has a frequency in the ultrasound area of between about 20 to 40 kHz.

4. The method of claim 1, wherein said pressure wave has a frequency in the infrasound area of below 20 Hz.

5. The method of claim 1, wherein the pressure wave generator is arranged on the patient in the form of an armband provided with said pressure wave generator being in transmissive communication with the patient.

6. Apparatus for detecting the condition of an access device providing access to a patient's blood vessel comprising an extracorporeal blood flow circuit for receiving said patient's blood including an introduction point for receiving said blood and an exit point for returning said blood to said patient's blood vessel via said access device, said extracorporeal blood flow circuit including a blood pump, the apparatus further comprising a pressure wave generator on the patient for generating a pressure wave on one side of said access device, and a pressure sensor for sensing said pressure wave on the other side of said access device in said extracorporeal blood flow circuit, and an indicating device for indicating the condition of the access device by analysing a signal sensed on the other side of said access device for substantial disappearance of the signal.

7. The apparatus of claim 6, wherein said pressure wave generator produces pressure waves having a frequency of between about 0.2 and 20 Hz.

8. The apparatus of claim 6, wherein said pressure wave generator produces pressure waves having a frequency in the ultrasound area of between about 20 to 40 kHz.

9. The apparatus of claim 6, wherein said pressure wave generator produces pressure waves having a frequency in the infrasound area of below 20 Hz.

10. The apparatus of claim 6, wherein said pressure wave generator is an armband provided with said pressure wave generator being in transmissive communication with the patient.

11. A method of detecting the condition of an access device providing access to a patient's blood vessel, said access device comprising an arterial needle for supplying blood from said patient's blood vessel to an introduction point in an extracorporeal blood flow circuit including a blood pump, and a venous needle for returning said blood from an exit point in said extracorporeal blood flow circuit to said patient's blood vessel, said method comprising:

generating a pressure wave in said extracorporeal blood flow circuit by the blood pump;

sensing pressure alterations produced by the pressure wave generated by the blood pump by a venous pressure sensor arranged between the venous needle and the blood pump in the extracorporeal blood circuit to produce an alternating venous pressure signal which is the sum of a first alternating pressure signal transmitted from the blood pump to the venous pressure sensor via the extracorporeal blood circuit and a second alternating pressure signal transmitted from the blood pump via the arterial needle, the patient's blood vessel and the venous needle to the venous pressure sensor;

analysing the alternating venous pressure signal; and indicating a changed condition of the access device at the disappearance of the second alternating pressure signal transmitted from the blood pump via the arterial needle, the patient's blood vessel and the venous needle to the venous pressure sensor.

12. The method of claim 11, wherein said pressure wave has a frequency of between about 0.2 and 20 Hz.

13. An apparatus for detecting the condition of an access device providing access to a patient's blood vessel, said access device comprising an arterial needle for supplying blood from said patient's blood vessel to an introduction point in an extracorporeal blood flow circuit including a blood pump, and a venous needle for returning said blood from an exit point in said extracorporeal blood flow circuit to said patient's blood vessel, said apparatus comprising:

a pressure wave generator comprising said blood pump in said extracorporeal blood flow circuit;

a venous pressure sensor arranged between the venous needle and the blood pump in the extracorporeal blood circuit for sensing pressure alterations produced by a pressure wave generated by the blood pump and for producing an alternating venous pressure signal which is the sum of a first alternating pressure signal transmitted from the blood pump to the venous pressure sensor via the extracorporeal blood circuit and a second alternating pressure signal transmitted from the blood pump via the arterial needle, the patient's blood vessel, and the venous needle to the venous pressure sensor;

an analysing and indication device for analysing the alternating venous pressure signal and indicating a changed condition of the access device at the disappearance of the second alternating pressure signal transmitted from the blood pump via the arterial needle, the patient's blood vessel and the venous needle to the venous pressure sensor.

14. The apparatus of claim 13, wherein said pressure wave generator produces pressure waves having a frequency of between about 0.2 and 20 Hz.

15. A method of detecting the condition of an access device providing access to a patient's blood vessel, said access device comprising an arterial needle for supplying blood from said patient's blood vessel to an introduction point in an extracorporeal blood flow circuit including a blood pump, and a venous needle for returning said blood from an exit point in said extracorporeal blood flow circuit to said patient's blood vessel, said method comprising:

sensing an alternating venous pressure wave by a venous pressure sensor arranged adjacent the venous needle between the venous needle and the blood pump in the extracorporeal blood circuit to produce an alternating venous pressure signal;

sensing an alternating arterial pressure by an arterial pressure sensor adjacent the arterial needle arranged between the arterial needle and the blood pump in the extracorporeal blood circuit to produce an alternating arterial pressure signal; and emitting an alarm signal when the proportion between the venous and arterial alternating pressure signals is changed substantially.

16. The method of claim 15, further comprising:

processing the venous and arterial alternating pressure signals to remove alternating pressure signals originating from said blood pump to obtain venous and arterial pulse pressure signals corresponding to the patient's heartbeat;

emitting an alarm signal when the proportion between the venous and arterial pulse pressure signals is changed substantially.

17. The method of claim 15, or 16, wherein the substantial change is a drop below 50% of an original value.

18. The method of claim 15, or 16, wherein the substantial change is a drop below 30% of an original value.

19. The method of claim 15, or 16, wherein the substantial change is a drop below 20% of an original value.

20. The method of claim 17, wherein the original value is the value of said proportion at the initiation of the extracorporeal treatment.

21. An apparatus for detecting the condition of an access device providing access to a patient's blood vessel, said access device comprising an arterial needle for supplying blood from said patient's blood vessel to an introduction point in an extracorporeal blood flow circuit including a blood pump, and a venous needle for returning said blood from an exit point in said extracorporeal blood flow circuit to said patient's blood vessel, said apparatus comprising:

a venous pressure sensor arranged adjacent the venous needle between the venous needle and the blood pump in the extracorporeal blood circuit for sensing an alternating venous pressure to produce an alternating venous pressure signal;

an arterial pressure sensor arranged adjacent the arterial needle between the arterial needle and the blood pump in the extracorporeal blood circuit for sensing an alternating arterial pressure to produce an alternating arterial pressure signal; and an alarm device for emitting an alarm signal when the proportion between the venous and arterial alternating pressure signals is changed substantially.

22. The apparatus of claim 21, further comprising:

processing means for processing the venous and arterial alternating pressure signals to remove alternating pressure signals originating from said blood pump to obtain venous and arterial pulse pressure signals corresponding to the patient's heartbeat;

an alarm device for emitting an alarm signal when the proportion between the venous and arterial pulse pressure signals is changed substantially.

23. The apparatus of claim 21, or 22, wherein the substantial change is a drop below 50% of an original value.

24. The apparatus of claim 21, or 22, wherein the substantial change is a drop below 30% of an original value.

25. The apparatus of claim 21, or 22, wherein the substantial change is a drop below 20% of an original value.

26. The apparatus of claim 23, wherein the original value is the value of said proportion at the initiation of the extracorporeal treatment.

* * * * *